United States Patent [19]
Pastre

[11] 3,944,669
[45] Mar. 16, 1976

[54] METHODS FOR CONTROLLING CANNIBALISM AND TAIL BITING IN PIGS

[75] Inventor: Maurice Pastre, Lyon, France

[73] Assignee: Pepro, France

[22] Filed: Feb. 12, 1974

[21] Appl. No.: 441,758

[30] Foreign Application Priority Data
Feb. 14, 1973  France .............................. 73.05851

[52] U.S. Cl. ................................. 424/232; 424/258
[51] Int. Cl.² ....................................... A61K 31/625
[58] Field of Search ............................ 424/232, 258

[56] References Cited
UNITED STATES PATENTS

| | | | |
|---|---|---|---|
| 2,799,615 | 7/1957 | Heymons ............................ | 424/258 |
| 2,802,771 | 8/1957 | Fields et al. ........................ | 424/258 |

OTHER PUBLICATIONS

Hutyra et al. – *Special Pathology & Therapeutics* (1938) Vol. III p. 242.

*Primary Examiner*—V. D. Turner
*Attorney, Agent, or Firm*—Robert E. Burns; Emmanuel J. Lobato; Bruce L. Adams

[57] ABSTRACT

Methods and compositions for controlling cannibalism and tail biting are disclosed containing 8-hydroxy quinoline as active material. They are particularly suitable for use in pigs.

3 Claims, No Drawings

METHODS FOR CONTROLLING CANNIBALISM AND TAIL BITING IN PIGS

FIELD OF THE INVENTION

This invention relates to methods and compositions suitable for controlling cannibalism and tail biting in pigs.

The compositions used with method of the invention are distinguished by the fact that they contain at least one hydroxy quinoline derivative as active material. In the context of the invention, the expression "at least one hydroxy quinoline derivative" covers hydroxy quinoline itself and the various derivatives of hydroxy quinoline specified hereinafter.

BACKGROUND OF THE INVENTION

Cannibalism and tail biting are two well-known manifestations of aggressiveness in pigs and sows.

The most frequent manifestation of cannibalism is the sow which eats its young. There are various causes for this phenomenon, including late transfer to the farrowing shed, farrowing pains, the presence of a noisy or unknown person, mastitis, etc. Cannibalism may also occur following changes in breeding conditions, mixing of litters, transportation, or in one and the same litter when a pig is attacked by its congeners.

Tail biting is common among young animals. All the pigs of one and the same sty progressively have their tails bitten by one or two congeners. The lesions caused always have serious consequences: the pig that has been bitten suffers, becomes timid and no longer takes food. The stub of the tail becomes infected and the resulting degeneration of the spinal cord can cause paralysis.

There are various reasons for tail biting. It can be caused by feed problems, including severe rationing, unappetising or unbalanced food, sudden changes in ration, disturbed timetables, lack of water, insufficient feeding troughs. Tail biting can also be caused by the particular ambient conditions prevailing: excessively bright light, noise, inspections, storms, inadequate ventilation, high temperature, humidity, lack of space, the introduction of an animal into an already existing litter, damp, cold bedding, etc.

Solutions to these problems that have already been proposed are either relatively ineffectual or too painful to the animal and, hence, prejudicial to its development.

Thus, it has been proposed either to cut the teeth of the young piglets or to cut their tails with forceps or with a rubber ring. It has also been proposed to apply theoretically repulsive products based on gas oil or on Norwegian pine oil, but unfortunately these products have no practical effectiveness.

THE INVENTION

It has now been found that the manifestations of aggression described above can be avoided by spraying a composition containing one or more hydroxy quinoline derivatives as its principal active material onto those parts of the animal capable of being attacked by its congeners.

The following compounds are examples of the 8-hydroxy quinoline derivatives which can be used for this purpose:
- 8-hydroxy quinoline and its organic salt such as its citrate, tartrate, sorbate, cinnamate;
- the double sulphate of 8-hydroxy quinoline and potassium;
- the sulphate of hydroxy quinoline and potassium;
- 5-chloro-8-hydroxy quinoline;
- 5,7-dibromo-8-hydroxy quinoline;
- 5,7-diiodo-8-hydroxy quinoline;
- 5-chloro-7-iodo-8-hydroxy quinoline;
- 5-nitro-8-hydroxy quinoline;
- 7-iodo-8-hydroxy quinoline-5-sulphonic acid and its alkali metal salts;
- the methyl sulphate of N-methyl-8-hydroxy quinolinium;
- 8-hydroxy quinoline iodo bismuthate;
- the 8-hydroxy quinoleate of bismuth or aluminium copper and zinc;
- 8-hydroxy quinoline benzoate;
- 8-hydroxy quinoline sulphathiazole phthalate;
- 8-hydroxy quinoline salicylate;
- 8-hydroxy quinoline-5-sulphonic acid and its heavy metal salts (aluminium, bismuth, copper, zinc);
- 8 hydroxy quinoline hydrochloride;
- phosphorus derivatives of 8-hydroxy quinoline.

The mechanism responsible for the repulsive effect of the compositions according to the invention is not known in any detail, although the results obtained have been extremely spectacular and unexpected, a property of this nature never having been described in the past.

To enable them to be conveniently used by the consumer, the above hydroxy quinoline derivatives will generally be formulated with suitable fillers and/or additives and, if necessary, with other active materials capable of complementing the activity of the products according to the invention.

The formulations used in the method of this invention will preferably be liquid formulations or solid formulations which can be diluted with water or in a suitable solvent before application.

The formulations can be in the form of aqueous solutions in cases where the hydroxy quinoline derivative used is sufficiently soluble in water.

They can also be made up in the form of wettable powders containing the active material in dispersion in an inert filler optionally admixed with a surfactant or with antilumping agents or deflocculants.

The following are examples of compositions according to the invention:

Composition A

| | | |
|---|---|---|
| neutral 8-hydroxy quinoline sulphate | | 200 |
| double sulphate of hydroxy quinoline and potassium | | 100 |
| water | q.s.f. | 1000 |

This composition is in the form of an aqueous solution which is ready for use.

Composition B

| | |
|---|---|
| 5-nitro-8-hydroxy quinoline | 100 |
| 8-hydroxy quinoline sulphathiazole phthalate | 50 |
| 8-hydroxy quinoline salicylate | 50 |
| inert filler | 800 |

Composition C

This composition is particularly suitable for animals which have already been affected and in which it is desired to obtain a curative (disinfecting and healing)

effect on the wounds in addition to the repulsive effect. The composition is as follows:

| | | |
|---|---|---|
| 8-hydroxy quinoline iodo bismuthate | | 100 |
| basic aluminium salicylate | | 100 |
| water | q.s.f. | 1000 |

Composition D

| | |
|---|---|
| hydroxy quinoline sulphate | 15 % |
| tranquiliser marketed under the Trade Mark ALAMASK CPMN X | 20 % |
| nonyl phenol (surfactant) | 0.5 % |
| water | 64.5 % |

Composition D was sprayed onto a group of pigs affected by tail-biting which, for 1 month previously, had been unsuccessfully subjected to various treatments with products based on fuel or Norwegian pine oil.

Immediately after treatment, the pigs stopped attacking their congeners. The composition retains its activity for about 15 days.

I claim:

1. A method for controlling cannibalism and tail biting in pigs which comprises the step of applying, to the external surfaces of the pigs, a composition comprising an effective amount to prevent tail biting and cannibalism of an 8-hydroxy quinoline compound selected from the group consisting of at least one of 8-hydroxy quinoline; the double sulfate of potassium and 8-hydroxy quinoline; the neutral sulfate of 8-hydroxy quinoline; the salicylate, citrate, tartrate sorbate and cinnamate of 8-hydroxy quinoline; 5 nitro-8-hydroxy quinoline; 8-hydroxy quinoline sulfathiazole phthalate; 2-iodo-8-hydroxy quinoline-5-sulfonic acid and the 8-hydroxy quinolinate of bismuth, aluminum, copper or zinc.

2. The method according to claim 1 wherein said compound is combined with a compatible vehicle.

3. The method according to claim 1 wherein said composition is sprayed onto the pigs.

* * * * *